United States Patent [19]

Masuda et al.

[11] Patent Number: 4,472,498

[45] Date of Patent: Sep. 18, 1984

[54] ANALYSIS FILM AND A METHOD OF ANALYSIS USING THE SAME

[75] Inventors: Nobuhito Masuda; Yukio Yasuda; Shigeru Nagatomo; Hajime Makiuchi; Masaki Okazaki, all of Kanagawa, Japan

[73] Assignee: Fuji Photo Film Co., Ltd., Kanagawa, Japan

[21] Appl. No.: 401,771

[22] Filed: Jul. 26, 1982

[30] Foreign Application Priority Data

Jul. 24, 1981 [JP] Japan ................................ 56-116827

[51] Int. Cl.³ ...................... G01N 33/54; G01N 33/78
[52] U.S. Cl. .......................................... 435/7; 422/56; 422/57; 435/805; 436/500; 436/527; 436/537; 436/810; 436/815
[58] Field of Search .................... 435/7, 805; 422/56, 422/57; 436/810

[56] References Cited

U.S. PATENT DOCUMENTS

| 4,337,065 | 6/1982 | Hiratsuka | 422/56 X |
| 4,340,564 | 7/1982 | Harte | 422/57 X |
| 4,362,697 | 12/1982 | Tabb | 422/57 X |
| 4,363,874 | 12/1982 | Greenquist | 422/57 X |

*Primary Examiner*—Sidney Marantz
*Attorney, Agent, or Firm*—Sughrue, Mion, Zinn, Macpeak & Seas

[57] ABSTRACT

An analysis film comprises a reagent layer composed of a porous material which contains an antibody but does not substantially contain a complex of an analyte or a labelled antigen with the antibody. In the analysis film, reagents for enzyme immune reaction of homogenous type are incorporated so that an analyte is analyzed without requiring B/F separation. An analysis method for various analytes using the same provides high sensitivity, high accuracy as well as good reproducibility and is simple and rapid.

19 Claims, 6 Drawing Figures

ANALYSIS FILM AND A METHOD OF ANALYSIS USING THE SAME

BACKGROUND OF THE INVENTION

Field of the Invention

This invention relates to a method for the measurement of the concentration of a substance which plays an important biochemical role or of various substances derived from a living body (hereafter "analyte") using a protein capable of specifically binding the substance through competitive reaction. This invention further relates to an analysis film comprising a reaction layer—where the aforesaid analyte is competitively reacted with a protein capable of specifically binding the same—and a signal is formed by undergoing a change in proportion to concentration of the analyte is received. The term "signal" refers to a detectable change that is directly or indirectly indicative of the presence and/or concentration of a substance being analyzed, i.e., the analyte, or a reaction or decomposition product of the analyte.

DEVELOPMENT OF THE INVENTION

In clinical analysis, various methods where several reagent solutions are added to a sample liquid and the concentration of an analyte in the sample liquid is measured are known. In these methods, reaction reagents must be accurately weighed and thoroughly mixed in order to improve the reproducibility of the measurement results and, sometimes, precipitates must be separated from supernatants by centrifugal techniques, which requires high skill.

To replace such conventional methods, devices which provide high reproducibility without requiring high skill by automating all such procedures have been developed, particularly in the field of clinical analysis using solutions, i.e., in "wet analysis". Such devices are convenient for measuring large numbers of sample liquids. However, wet analysis techniques require complicated handling of solutions and, correspondingly, require an analytical device including complicated transportation means. Further, such devices for wet analysis have the serious disadvantage of high expense. In addition, cleanliness of a high level must always be maintained to prevent contamination during analysis or to prevent sample liquids from contaminating each other. These procedures also require high skill.

In place of such conventional wet analysis techniques, dry multilayer analysis elements in which reaction reagents are incorporated have been proposed as a simple analysis means where the supply of reagent solutions is not substantially required so that high skill is not required. Such multilayer analysis elements are advantageous in that they are inexpensive as compared to the automated devices described above. Multilayer analysis films for dry procedures suited for automated chemical analysis are described in, e.g., Japanese Patent Publication No. 21677/78 (corresponding to U.S. Pat. No. 4,042,335). Using such multilayer analysis films, dry analysis procedures which do not involve chromatographic phenomenon in an analysis tape obtained by impregnating filter paper with reagent solutions (a classical analysis material for dry procedures) has been enabled. These multilayer analysis films are characterized in that they are extremely inexpensive as compared with conventional automated analytical devices for wet procedures and are suited for analysis of albumin, bilirubin, etc., in blood serum.

In the case of using multilayer analysis materials utilizing known chemical reactions or enzymatic reactions, including the multilayer analysis film described in Japanese Patent Publication No. 21677/78, however, it is difficult to measure a component in trace amounts or a component having high structural specificity.

Accordingly, in practice analytical techniques using wet procedure has still been applied to the analysis of such a component. One representative analysis method that to date must rely on wet analysis where expensive apparatus is required is a system which utilizes an immunological reaction.

When attempts have been made to apply immunological reactions to conventionally known multilayer analysis films, it has proven difficult to obtain satisfactory analytical results due to problems inherent in immulogical analysis, which will be later described. Further, immunological measurements used in known multilayer analysis films utilize heterogenous competitive reactions involving liquid phase reactions which require B/F separation.

Specifically, in heterogenous immunological reactions which as are conventionally practiced the reagents used comprise (a) a labelled analyte being measured (or an analogue thereof) which is chemically bound to a label such as a dye, fluorescent substance, enzyme, etc., which possess a detectable signal; and (b) a protein having a specific, binding capability common to the labelled analyte or analogue thereof (a specific binding protein, generally an antibody). In actual reaction, an analyte and the labelled analyte competitively react with the specific binding protein. As a result, either the amount of the label in the conjugate (B) bound to the specific binding protein or the amount of the labelled analyte (F) in the free state (i.e., not bound to the specific, binding protein) represents the amount of analyte present.

In measuring the label, it is practically impossible to obtain measurement data on the bound, labelled conjugate (B) alone independently from the free labelled analyte (F) or vice versa. Therefore, the conjugate (B) having the labelled analyte bound to the specific binding protein must necessarily be separated from the free labelled analyte (F) through B/F separation, prior to analysis. Alternatively, a particular design is required so that no signal is substantially produced either from the labelled analyte bound to the specific binding protein, i.e., the conjugate (B), or from the free labelled analyte (F). Even though either is adopted, such involves difficulties in layer structure, means for imparting various functions to respective layers, selection of raw materials composing these layers, etc., to introduce such particular reactions into multilayer analysis elements for a dry procedure. If the aforesaid design is to be realized, a serious reduction in sensitivity is unavoidable.

On the other hand, measurement of a component having high structural specificity or a component in trace amount, including measurement of an analyte utilizing an immune response, involves the inherent problem that reaction sufficient to generate a signal change occurs only with difficulty, unless a large amount of sample liquid is employed. For example, to detect glucose in serum, a very small amount of a sample liquid is generally sufficient; however, a sample liquid of from about 25 to about 100 $\mu$l is generally required for measurement of an analyte utilizing an immune response. In analysis utilizing an immune response that requires a large amount of a sample liquid as compared to the amount of a sample liquid for conventional measurement, it is also necessary that the immune reaction sufficiently proceed to an extent that a change or modulation of a detectable signal results.

For analysis utilizing an immune reaction, which requires particular considerations, techniques developed for analysis utilizing other reactions are not applicable thereto as they are. Referring to one example, the most serious problem in adopting technique for conventional wet type analysis to multilayer analysis films was a localized high density which occurred in dropping or spotting a sample liquid onto the analysis film. This phenomenon is a chromatographic phenomenon and, due to this non-uniform density distribution, a relationship between the amount of the analyte being measured and a change or modulation in a detectable signal is impaired. To obviate such disadvantage, technical efforts with respect to dry type multilayer analysis films concentrated on the point of to how a sample liquid could be uniformly distributed. In known multilayer analysis films, however, the aforesaid problems inherent in analysis utilizing an immune reaction were not recognized, and accordingly, it is questionable as to whether multilayer analysis films suited for other types of analysis—which merely require a smaller amount of sample liquid—could be effectively employed for the analysis utilizing an immune reaction.

Taking the aforesaid chromatographic phenomenon into account, it was assumed in the art that chromatographic phenomenon would adversely affect analysis involving an immune reaction which required a large amount of sample liquid. More seriously, destruction of a sample liquid in the lateral direction one measure to avoid chromatographic effects, is directly linked with subsequent, immediate diffusion and mobilization in the thickness direction; accordingly, such is contrary to the requirement of analysis utilizing an immune reaction that a time period sufficient for effecting the immune reaction must be available.

In Japanese Patent Publication No. 21677/78, a multilayer analysis element comprising a development layer of a non-fibrous porous material and a reagent layer in which a medium such as gelatin or PVA is impregnated with a reagent is disclosed. However, the volume of sample liquid that can be absorbed in a short period of time is merely several (2 or 3) $\mu l$ to 20 $\mu l$ per 1 cm$^2$ in the case of using isotropically porous materials such as "blush" polymers (cellulose acetate polymers, etc. prepared in a manner as described in U.S. Pat. No. 3,992,158 which are isotropically porous, i.e., possess pores in all directions) as are normally available or colloidal materials such as gelatin. Such materials absorb 25 $\mu l$ to 300 $\mu l$ of a sample liquid necessary for immunological analysis in a short period of time only with difficulty. Accordingly, detection sensitivity is poor.

In addition, a multilayer analysis elements formed by laminating, in order, a spreading layer of a non-fibrous porous material, a reagent layer containing an interactive substance which gives a diffusible chemical species which can be detected, a light shielding layer, a detection layer and a transparent support have also been suggested (Japanese Patent Application (OPI) No. 40191/76; the term "OPI" as used herein refers to an unexamined application which was open to public inspection). However, non-fibrous porous materials employed for such analysis elements do not give sufficient water retainment in a short period of time; thus, such analysis elements also involve the disadvantage that only analytical data of poor sensitivity are obtained.

Further, in Japanese Patent Application (OPI) No. 24576/81, a multilayer analysis element comprising a transparent support, a reagent layer obtained by incorporating reagents into colloidal substances and a fibrous porous carrier layer to eliminate interfering substances in a sample liquid is disclosed. However, incorporation of reagents (proteins capable of effecting specific binding) seriously inhibits the binding reaction with components effective for measurement so that poor detection sensitivity or a reduction in accuracy results.

A multilayer analysis film that is intended for use with an immunological reaction taking the inherent properties of immunological analysis into account is also known, as stated above.

For example, the invention described in Japanese Patent Application (OPI) No. 90859/80 (corresponding to EPC Publication No. 0013156) is characterized in that thermally stable organic polymer particles are adhered point-to-point using an adhesive comprising an organic polymer different from the aforesaid polymer particles and the thus formed three-dimensional particulate structure is used as the porous material layer described above. However, it is extremely difficult to prepare such a special material and such is also expensive. In addition, a disadvantage is that if the thickness of the particulate structure is increased to enable 25 $\mu l$ or more of a sample liquid necessary for immunological analysis element containing the particulate structure, surface smoothness is seriously lowered so that upon dropping or spotting, measurement accuracy of optical density is decreased.

In Japanese Patent Application (OPI) No. 131089/78, a multilayer analysis element comprising a reagent layer having previously incorporated therein an immunologically bound pair (antigen-bound antibody) or immunological complex and a layer for receiving diffused species provided thereunder is disclosed. In using this element, when a drop of a sample liquid is dropped or spotted on the reagent layer, a substitution-release type immunologically competitive reaction occurs between a known amount of an immunologically bound pair (labelled antigen-bound antibody) previously present in the reagent layer and an analyte in the sample liquid and, a released species which acquires diffusibility as a result of immunological reaction is diffused into the layer to receive the diffused species, the released species being optically measured. However, in this method, in which an unknown amount of antigen in a sample liquid is mutually reacted with a labelled antigen-bound antibody to thereby release a labelled antigen, the release occurs very slowly and, as a result, the detectable diffusible species is released in an extremely small amount which results in markedly poor sensitivity and poor response. In particular, in the case of a component having a molecular weight of several thousand (e.g., insulin has a molecular weight of about 5,600), a calibration curve which is far from a standard calibration curve can only be obtained, even if incubation is conducted for 24 to 48 hours. This technique is not suitable for rapid assay.

In general, a method in which an antigen in a sample liquid and a labelled antigen are competitively reacted with an antibody at the same time through immunological reaction using liquid reagents, or a method comprising primarily reacting an antigen and an antibody in a sample liquid, provide much higher sensitivity. For such methods, it is required that a reaction layer having contained therein a labelled antigen (or an antibody) be separated from a reagent layer having contained therein an antibody (or a labelled antibody) instead of using a labelled antigen-bound antibody. In this case, reagents in the reagent layer are dissolved out with a sample liquid and substantially freely diffused into the reaction layer, where the reagents cause a competitive antigen-antibody reaction with an antibody or antigen, of an unknown amount contained in the sample liquid.

As a result of extensive studies on the efficiency of various analysis films using various reagents, we noted that in order to overcome the foregoing problems it is effective (1) to employ reagents for enzyme immunoassay of an homogeneous type which requires no B/F separation and (2) to selectively choose materials for the reaction layer.

SUMMARY OF THE INVENTION

The multilayer analysis element in accordance with this invention is a dry type analysis element suited for quantitative analysis of an analyte utilizing a specific protein binding reaction and an enzyme reaction of an homogeneous type as described above.

One object of this invention is to provide a dry type multilayer analysis element which involves simple and rapid operation and has high sensitivity, high accuracy and excellent reproducibility.

We noted that in order to maintain high sensitivity and reproducibility comparable to prior art immunological assay methods (which involve accurately weighing a sample liquid and mixing the same with reagents to effect reaction), permit simple operation without requiring high skill—characteristic of dry type analysis, in combination with high sensitivity and high reproducibility, it is necessary for at least 25 $\mu$l, desirably 50 to 200 $\mu$l, of a sample liquid to participate in a competitive immune reaction, as in prior art wet type methods in which a sample liquid is weighed and mixed with reagents to cause an immune reaction. The amount "at least 25 $\mu$l" is a considerably large amount as compared to the amount of analyte measured in conventional dry type multilayer analysis films which generally utilize chemical reactions other than immune response and, accordingly, such conventional analysis films cannot be employed for purpose of immunological examination as they are.

Based upon the foregoing, we found that a fibrous or non-fibrous porous medium is appropriate as a reaction medium which possesses cavities capable of absorbing at least 25 $\mu$l of a liquid sample.

The analysis film in accordance with this invention is basically composed of a reaction layer of a fibrous or non-fibrous porous medium, in which reagents for specific protein binding reactions of an homogeneous type that have not been heretofore used in to conventional multilayer analysis elements of the dry type are incorporated in the reaction layer. More particularly, the reaction layer:

(1) comprises a fibrous and/or non-fibrous porous material;

(2) contains a protein capable of specifically binding a labelled substance capable of modulating an amount of a detectable signal produced through enzyme reaction, as a result of a binding reaction to the specific protein and an analyte; but (3) does not substantially contain any complex of the analyte, analogues thereof or the labelled substance, with the specific protein.

Figure 1:
FIG. 1 is a schematic cross-sectional view showing an embodiment of an analysis element in accordance with this invention.
Figure 2:
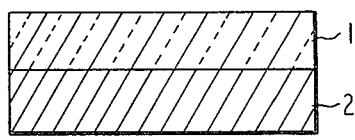
FIGS. 2 to 6 are, schematic cross-sectional views showing preferred embodiments of an analysis element in accordance with this invention which is composed of a plurality of layers.
Figure 3:
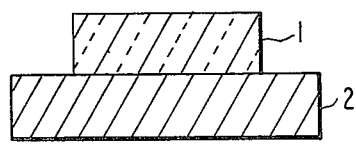
Figure 4:
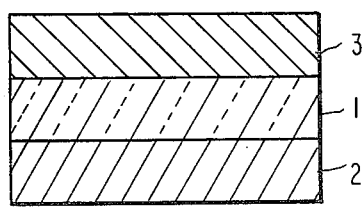
Figure 5:
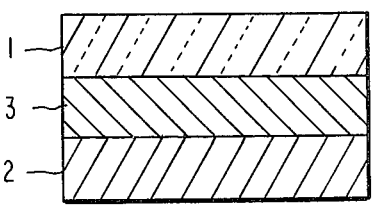

In the Figures, the numerals mean:
1: reaction layer
2: detection layer
3: reagent layer
4: light-shielding layer
5: water-absorbing layer
6: support

PREFERRED EMBODIMENTS OF THE INVENTION

The analysis film comprising the aforesaid reaction layer according to this invention contains reagents for specific protein-binding reactions of an homogeneous type which does not require B/F separation subsequent to reaction. Therefore, merely by dropping or spotting a sample liquid or a mixture thereof with other reagents onto the reaction layer a modulated detectable signal can be obtained, and this signal is detected in a manner suited to the label employed, as will be later described.

The term "homogeneous type" as used herein refers to a type of competitive binding reaction in which a labelled bound species (e.g., a labelled antigen-bound antibody) is distinquishable from a labelled free species (e.g., a labelled antigen) and thus no B/F separation is required; the term is used as opposed to the term "heterogeneous type" which refers to a competitive binding reaction in which B/F separation is always required since a labelled bound species is not distinguishable from a labelled free species.

The term "modulate" is used to mean to change or vary intensity or tone of, e.g., enzyme activity, in proportion to the amount of an analyte, and thus includes to intensify, weaken, appear or disappear enzyme activity after a competitive binding reaction, as will later be described in detail with reference to representative Types (1) to (4).

The term "a protein capable of specifically binding both (a) a labelled substance capable of modulating an amount of a detectable signal and (b) an analyte" is often referred to as "a specific binding protein" or "a specific protein" which refers to a protein capable of specific combination with a substance that elicits a specific binding immune response when introduced into the tissues of an animal, and carries binding sites that link with the corresponding determinant.

In the analysis film of this invention only the reaction layer is mandatory; where a competitive binding reaction of homogenous type is carried out and a modulated detectable signal produced as a result of the binding reaction is detected. In this case, a function of allowing to proceed with the specific protein-binding reaction can also be composed as a separate layer, in accordance with the representative homogeneous immunological reactions hereafter described, from a layer having the function of receiving and detecting the detectable signal produced through the specific protein-binding reaction.

In such a case, the analysis film of this invention comprises the aforesaid reaction layer having laminated thereon or thereunder a reagent layer comprising a porous medium which contains the reagents for detecting the modulated detectable signal. Further, there may also be provided a detection layer in which a known reagent system for the detection of another detectable signal is incorporated, in which case the produced detectable signal is subjected to a conventional enzyme or chemical reaction as later described to convert the detectable signal into another detectable signal.

In any case, a support transparent to optical measurement can be used, if desired or necessary. The layer structure in this case results in a support having laminated thereon, if desired or necessary, a detection layer, and a reagent layer and/or a reaction layer, which then constitute an integral type multilayer analysis film.

The term "detectable signal" as used herein refers to a factor of an analyte in a sample liquid and is produced dependent upon the amount of a complex bound to a labelled substance (B) or a free labelled substance (F) induced as the result of a competitive reaction caused in the presence of a definite amount of a protein specifically binding to the analyte component, and a fixed amount of a labelled substance of the analyte component or an analogue(s) thereof which is also reactive with the specifically binding protein described above and is amenable to optical measurement.

The term "analyte component" refers to the same component as an analyte being analyzed; when thyroxine is an analyte (its concentration is thus unknown), a given concentration of thyroxine is used as the analyte component. Throughout the specification, however, the term "analyte component" is often simply referred to as "an analyte" usually accompanied by "labelled" or other distinghuishable wording.

The term "analogue" is used to refer to an analyte component that is usually chemically modified due to improving reactivity with a label but maintains its specific binding site thereon that binds specifically with its corresponding determinant.

Reagents for enzyme immunoassay of the homogeneous type employed in this invention are proteins capable of specifically binding to an analyte in a sample liquid (in general, an antibody, specifically binding protein, etc.), the analyte component or analogue thereof labelled with an enzyme which takes part in reaction(s) for producing a signal, a precursor of the signal, an enzyme or component which modulates enzyme activity (e.g., inhibitors, co-enzymes, secondary enzymes for purpose of converting concentration of enzyme substrate, etc.), etc.

The aforesaid reagents for enzyme immunoassay of the homogeneous type are well known in wet type analysis, along with the mode of immunological reaction in which each of the reagents participates. That is, competitive immunological reactions per se related to the reaction reagents incorporated in the integral type analysis film of this invention are known, and accordingly, detailed mechanisms of specific protein-binding reactions are not mentioned herein; depending upon the progress of each reaction, one skilled in the art would pay his attention appropriately to technical consideration.

It is common to employ, as reagents for enzyme immunoassay, a plurality of reagents depending upon the respective steps involved in the reactions concerned; however, some reagents should be stored separately from each other until the reaction desired is initiated and should be mixed only when a reaction desired is to be initiated. Reagents that should be handled in such a manner are well known in relation to immune reaction involving an enzyme, and, in wet type analysis, are stored in separate containers. Per this invention, enzyme immune reactions developed for use in wet type analysis are principally used and as a result, reagents which should be kept out of contact prior to reaction initiation are incorporated in separate layers. In the case of using the analysis film of this invention, however, it is unnecessary to take a time period between various reactions into account as critically as with wet type analysis, rather, it is sufficient if enzyme reaction (e.g., contact of an enzyme with a substrate) and specific protein-binding reaction (contact of an antigen with an antibody) are caused at least at the same time. Of course, it is preferred that immune reaction be first effected and followed by enzyme reaction. From such preference, which is common general knowledge in view of reaction mechanisms, it is preferred that an enzyme and its substrate be incorporated in separate layers and not be in the same layer. It is also preferred, for the same reason, that a labelled substance (e.g., labelled antigen) which is in a competitive relationship with an analyte (e.g., antigen) be in a separate layer from a layer containing a protein (e.g., antibody) having specific binding capability to the analyte and the labelled substance. For the same reason, it is desired that enzyme be incorporated in a layer separate from a layer containing an inhibitor, a prosthetic group or an allosteric effector.

To enhance analysis efficiency and sensitivity, generally a labelled substance (e.g., labelled antigen) should be incorporated in a layer as close as possible to an analyte (that is, the reagent layer in a basic embodiment of this invention, not the reaction layer). Accordingly, a protein having specific binding capability to the labelled substance (e.g., labelled antibody) is generally incorporated in other layers (in the above embodiment, in the reaction layer).

Hereafter, an outline of the course of a representative reaction system involved in an analysis film of this invention is described with reference to the structure of the analysis film per this invention.

In case that the analysis film is composed of a plurality of layers, basic principles for separate incorporation of the aforesaid reagents into these layers are:

(i) A specific binding protein is incorporated in a porous medium and a labelled substance is incorporated in a layer separate from the layer containing the specific binding protein.

(ii) Enzyme is incorporated in a layer separate from a layer containing an inhibitor and/or substrate.

(iii) A prosthetic group and an allosteric effector used in Type (3) and/or Type (4) below are handled as in the inhibitor; that is, enzyme is incorporated in a layer separate from a layer containing a prosthetic group or an allosteric effector.

As long as the principles are satisfied, reagents involved in the specific binding reaction can be incorporated in any of layers where the analysis film of this invention is composed of multiple layers.

TYPE (1)

In the case that the label of the aforesaid labelled substance is an enzyme which produces a signal and its enzyme activity is modulated through a coupling reaction with a protein which specifically couples with the analyte, a complex of a specifically binding protein and an analyte component labelled with an enzyme, or analogue thereof, an enzyme substrate which produces a signal by the action of the enzyme, and the like are incorporated into the reaction layer and the reagent layer. In this case, it is desired that the enzyme be incorporated in a layer separate from a layer containing the substrate, as described hereinabove. For example, in case that the analyte component labelled with the enzyme or analogue thereof is incorporated in the reagent layer, it is preferred that the specifically binding protein and the substrate be incorporated in the reaction layer. In the reaction system described above, a change or modulation of enzyme activity can similarly be realized using a selective inhibitor, even in the case that a change or modulation of enzyme activity is not induced by a specific protein binding reaction. For example, note the case where enzyme activity is modulated using inhibitors having different inhibition degrees against the enzyme in the specifically binding protein complex produced after the specific protein binding reaction and against the free enzyme-labelled substance. In this case, generally the inhibitor is incorporated in a layer separate from a layer containing a substance labelled with enzyme or specifically binding protein.

Specific examples of the aforesaid analyte component labelled with an enzyme or analogue(s) thereof which is effective for competitive immune reaction of this type and synthesis examples thereof are described in U.S. Pat. Nos. 4,040,907, 4,043,872 and 4,191,613, Japanese patent application (OPI) Nos. 5491/73 and 106724/76, etc. Use of inhibitors is described in detail in Japanese patent application (OPI) No. 20134/79.

Reactions which belong to Type (1) are illustratively shown by the following schemes wherein E is an enzyme, Sub is a substrate for the enzyme, SP is a specific protein, analyte-E is an enzyme-labelled analyte and SP-analyte-E is an enzyme-labelled analyte-specific protein complex; hereafter the same.

Type (1)-a:

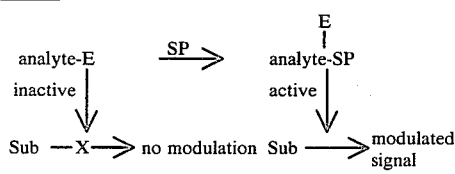

Type (1)-b:

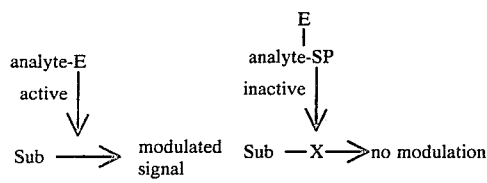

Type (1)-c:

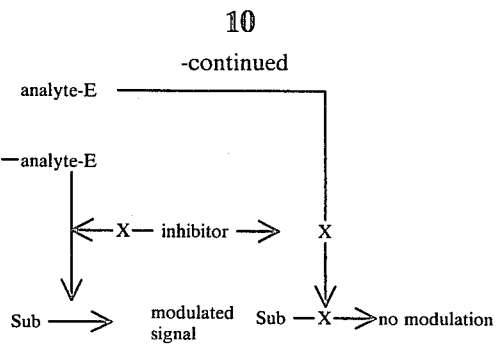

In the case where the analysis film is of plural layer type, a specific protein and a substrate are incorporated in a reaction layer, based on the basic principles for separate incorporation, on which a reagent layer containing a labelled substance (generally, a labelled antigen) therein is provided separately; alternatively, the analysis film is composed of a reaction layer containing a specific protein (generally, an antibody) having provided thereon, in sequence, a first reagent layer containing a substrate and a second reagent layer containing a labelled substance; etc. When an inhibitor is involved, the analysis film is composed of, for example, a reaction layer containing a specific protein having provided thereon, in sequence, a first reagent layer containing a labelled substance and a second reagent layer containing an inhibitor (or a substrate); in the case of incorporating the substrate in the second reagent layer, the inhibitor is externally supplied, e.g., by dropping it on the analysis film. As far as the basic principles for separate incorporation are followed, the second reagent layer can contain a labelled substance and the first reagent layer can contain an inhibitor (or a substrate).

TYPE (2)

In the case that the aforesaid labelled specific component is an inhibitor of an enzyme which participates in reactions for producing a signal, initial inhibiting activity is modulated by binding reaction between the specific component and a specific binding protein (e.g., antibody) so that the total activity of the enzyme is modulated and the thus modulated signal is detected. In such a system, a specific binding protein, an enzyme(s) for producing a signal, an analyte or analogue thereof labelled with an inhibitor(s) of the enzyme(s), an enzyme substrate(s) for producing a signal, etc. are incorporated in the reaction layer or in the reagent layer.

In the case that a substance labelled with an inhibitor and a substrate are incorporated in the reagent layer, the specific binding protein and enzyme are incorporated in the reaction layer. In the case that a substance labelled with an inhibitor alone is incorporated in the reagent layer, the layer structure can also be designed in such a manner that the reaction layer is divided into two layers; the specific binding protein and substrate are incorporated in a first reaction layer adjacent the reagent layer and, in a second reaction layer, enzyme is incorporated.

Specific examples of these reagents and syntheses thereof are described in detail in U.S. Pat. No. 748,005, Japanese patent application (OPI) Nos. 104896/80, 105291/78 and 115814/78, etc.

A representative reaction is illustratively shown below wherein analyte-inhibitor represents an inhibitor-labelled analyte, SP-analyte-inhibitor represents an inhibitor-labelled analyte-specific protein complex, and SP, E and Sub are the same as defined above.

Type (2):

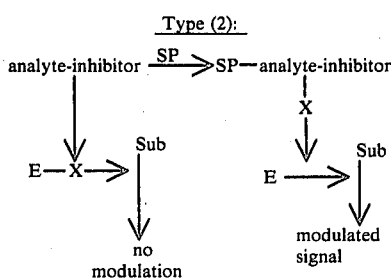

TYPE (3)

With a system which utilizes the characteristic that enzyme activity is markedly exhibited by binding of conjugated enzyme with a prosthetic group (a substance that must be loosely associated with an enzyme for the enzyme to function, e.g., coenzyme) for the first time, the prosthetic group is replaced by the foregoing inhibitor and total enzyme activity is modulated likewise; therefore, the system measurement is based upon the modulated signal. In such a system, a specific binding protein, an analyte component or analogue thereof labelled with the prosthetic group, an apo enzyme for producing a signal, an enzyme substrate for producing a signal, etc. are employed. Further, substances which do not belong to prosthetic groups but are known to be allosteric effectors—which can alter enzyme activity, either by intensifying (called (+) effectors) or by weakening (called (−) effectors) can also be employed for the purpose described above.

Representative reactions of Type (3) are illustratively given below wherein PG is a prosthetic group and the remaining indications are the same as defined above or defined in a similar manner.

Type (3)-a:

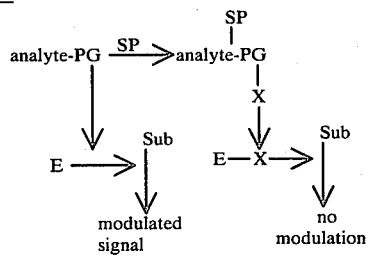

Type (3)-b:

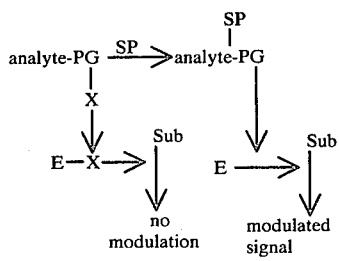

Among reagents described in Japanese patent application (OPI) Nos. 2997/80 and 146295/76, reagents that are disclosed to be suited for homogenous systems are effectively employed.

In the case of the analysis film of multilayer type, layers are constructed so as to meet the basic principles for the separate incorporation.

TYPE (4)

Reagents for a homogenous system which are employed in a system where the concentration of a substance in an enzyme system producing a signal or the concentration of coenzyme in the enzyme system comprise a labelled specific component or a labelled binding protein and, the local concentration of the enzyme or coenzyme described above is modulated by a specific binding reaction of these labelled substances. In response thereto, the amount of the signal produced modulations, e.g., an enzyme channeling system, can also be employed effectively as reagents in this invention. Examples of these reagents and preparation thereof are described in detail in Japanese patent application (OPI) No. 136896/79.

Representative reactions of Type (4) are illustratively given below wherein $E_1$ and $Sub_1$ are a first enzyme and a substrate for the first enzyme, respectively; $E_2$ and $Sub_2$ are a second enzyme and a substrate for the second enzyme; analyte-$E_1$ and analyte-$Sub_1$ are first enzyme- and substrate (for the first enzyme)-labelled analyte, respectively; and SP-$E_2$ is a second enzyme-labelled specific protein:

Type (4)-a:

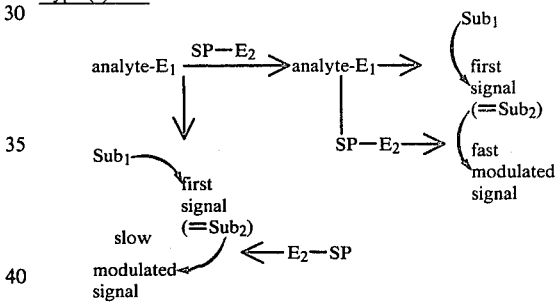

Type (4)-b:

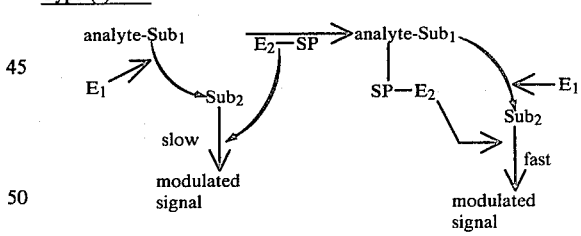

Various reagents for immunoassay of the homogeneous type described above are advantageous in that no B/F separation is required, as compared to conventional immunoassay of the heterogeneous type. In addition, the total amount of signal produced is correlated to the concentration of a specific component being analyzed and, as a result, measurement per se is simple and can be automated in a simple manner. These reagents are also advantageous in that no fixation of a specific binding protein is required, since no B/F separation is required. This results in the advantage that chemical modification, which is almost mandatory for immunoassay of a heterogeneous system, becomes unnecessary. Such is beneficial for preparation of reagents or for biological activity. However, in order to incorporate these reagents into an analysis sheet of the dry film type, various difficulties would be encountered. For example, conditions for effecting both immune reaction and enzyme reaction in a drop of a sample liquid of a limited volume are very specific, interfering materials in a sample liquid must be eliminated, a definite amount of a reagent(s) per unit area must be used while maintaining the activity thereof, etc.

The analysis element of this invention constructed as described above provides high sensitivity and high reproducibility since the amount of sample liquid necessary for competitive immunological reaction can be retained in the reaction layer. In addition, the analysis element of this invention enables analysis which is completed in an extremely short period of time in a very simple operation without particular high skill.

The analysis element of this invention can be of any shape so long as analysis can be effected, but, in general, a sheet-like or film-like shape is preferred.

The multilayer analysis of this invention can be employed, for example, as described below.

An analyte (for example, antigen or antibody) in a sample liquid and a labelled analyte component (for example, labelled antigen or antibody) react with a specific binding protein (for example, antibody to antigen or antigen to antibody)—which specifically recognizes and binds to the antigen or antibody—to produce an immunological complex (usually at temperatures of from 0° to 56° C., preferably 10° to 45° C. for 1 minute to 24 hours, under normal pressure; conditions vary depending upon kind of analyte, mode of reaction involved and layer structure). The proportion of free, labeled analyte component to bound, labelled analyte component which participates in binding to the specific binding protein becomes a factor of the analyte in the sample liquid, and the total activity of the enzyme system producing a signal is determined and a signal is correspondingly produced. The signal is then optically measured. On the other hand, based upon the amount of the signal obtained corresponding to a given amount of analyte component, a calibration curve is previously prepared. By comparison to this calibration curve, the analyte (specific component) is quantitatively determined.

The above description is for the case where a detectable signal is produced directly from an enzyme reaction; in this invention, however, the signal produced is not limited to a signal that is directly detectable. In such a case, i.e., where a signal is not per se detectable as it is, the signal should be converted into another secondary signal, for example, hydrogen peroxide in glucose analysis, a leuco compound in the case of labeling an analyte component with a leuco dye, or a conventional enzyme reaction(s) or chemical reaction(s) should be applied to such a signal (which be considered a "signal precursor") to thereby produce a detectable signal. For example, in glucose analysis, hydrogen peroxide (a primary signal or signal precursor) formed is further reacted with a reagent composition comprising peroxidase, a hydrogen donor and a coupler, thereby the hydrogen peroxide is converted into a colored product. Reagents used for this purpose can appropriately be incorporated into the reaction layer or into a detection layer which is optionally provided separately from the reaction layer.

In this invention, an analyte (specific component) is primarily detected by optical means. Therefore, it is desired that a light-shielding layer be provided to eliminate the possibility that interfering materials other than the analyte (specific component) being measured (e.g., erythrocytes or hemoglobin in the case of using whole blood as a sample liquid, or a fluorescenece-labelled or dye-labelled antigen or antibody, etc.) participate in the optical measurement. In general, the light-shielding layer is inserted between the reaction layer and the optionally provided detection layer; however, in the case where a light-shielding function is imparted to the reaction layer, the light-shielding layer can be omitted.

Typical examples of porous materials which can be used in the reaction layer include non-fibrous materials such as polymer filtering membranes—which are known membrane for filtering polymers—having a variety of pore sizes, Cephadex, agarose, dextran, etc.; natural fibers such as pulp, cotton, silk, wool, etc.; semi-synthetic fibers such as cellulose esters, viscose rayons, etc.; synthetic fibers such as polyamides, polyesters, polyolefins, etc.; fibrous inorganic materials, e.g., glass fibers, colored glass fibers, asbestos—in the form of a textile (fabric that is woven or knitted); felt (fabric of matted, compressed animal fibers obtained by applying heat, moisture or pressure), or non-woven cloth (fibers more closely joined to each other by chemical treatment or heating of fibers per se or fibers adhered to each other using an adhesive), etc.—or water-permeable paper, and the like.

Specific examples of membrane filters include Microfilter (made by Fuji Photo Film Co., Ltd.), Millipore (made by Millipore Corporation), etc. These membrane filters generally possess a pore diameter of about 0.2 to about 20 $\mu$m, preferably 0.3 to 5.0 $\mu$m, more preferably 0.5 to 1.2 $\mu$m.

A wide variety of fabrics can be employed as the reaction layer, and of various fabrics, plain weave, which is formed by weaving warp and weft yarns alternately, is preferably used. As for the warp and weft which comprise a plain weave, a desirable count ranges from 20 to 120. Of fabrics having a plain weave, cotton fabrics such as close cloth, canequim, broadcloth and poplin are preferably employed. In addition to other natural fibers woven in the same manner as the above described cotton fabrics (e.g., kapok, flax, hemp, ramie, silk and so on), fabrics obtained by weaving mixed yarns of synthetic fiber (e.g., viscose rayon, cupro-ammonium rayon, cellulose acetate, vinylon, polyethylene terephthalate and so on) and cotton fiber in the same manners as in the above described cotton fabrics, and fabrics obtained by weaving synthetic fiber yarn in the same manners as the above described cotton fabrics can be also employed.

The fibers described above can be used in the reaction layer in the form of a non-woven fabric molded into cloth form, not in textile form.

Paper which can be used in the reaction layer can be freely chosen so long as it is water permeable. More specifically, a filter paper giving voids of about 20 to about 90% can be used; particularly preferred is thin, fine filter paper. Indian paper or Japanese paper such as paper made of paper mulberry (Broussonetia kazinoki) or mitsumata (Edgeworthia papyrifera), etc. can also be employed. Not only natural cellulose paper but also synthetic paper (made of, e.g., polystyrene, polyester, polyethylene, polypropylene, etc.) obtained by paper-making fibers of synthetic high molecular weight substances—which possesses water permeability—can also be employed as materials for the reaction layer.

Further, the incorporation of fine particles (having a particle size of about 1 $\mu$m to about 1 mm, preferably 10 to 300 $\mu$m) of dextran, agarose, acrylamides, cellulose, etc., into these porous materials by intertwining the particles with these materials can increase water-retention capability of a sample liquid, which is advantageous.

It is preferred that the porous material possess voids of about 20 to about 90%, preferably 50 to 90%, while void percentage varies depending upon the kind of the porous material, pore size, etc. Void volume can be calculated with reasonable accuracy by a variety of techniques such as described in Chalkey, *Jounal of the National Cancer Institute,* vol. 4, page 47 (1943) and by direct weighing and determining the ratio of actual weight of the structure to the weight of solid material equal in volume to that of the structure, comparably composed of constituents from a structure.

Porous material having various pore sizes of about 0.2 to about 20 μm can be appropriately chosen depending upon the kind of an analyte. For example, in the case that analytes are low molecular weight substances such as insulin, drugs, etc. (these have a molecular weight of from about 200 to about 10,000), porous materials having a relatively small pore size are preferably used; if analytes have relatively high molecular weight as in immunoglobulins (molecular weight of which is about 160,000) or albumin (molecular weight of which is about 75,000), porous materials having a relatively large pore size are preferably used.

In the case where fine particles are incorporated in the porous material, the water-retention capability of the reaction layer can be further improved as a whole due to the water-retention capability of the fine particles while maintaining the porous nature of the reaction layer. Even in this case, the porous nature of the reaction layer as a whole should be maintained and, accordingly, the amount of fine particles that can be incorporated (preferably thoroughly mixed) can naturally be set forth. In general, the amount of fine particles is up to 90 wt% based on the total weight of the reaction layer.

To incorporate a protein capable of specifically binding a specific component into the porous materials containing fine particles, one can incorporate fine particles to which the protein described above has previously been bound into porous materials. Binding can be either chemically (in a manner as described in, e.g., P. Cuatrecasas, *J. Biol. Chem.,* vol. 245, pages 3059 to 3065 (1970), R. Axen et al., *Nature,* vol. 214, page 1302 (1967), P. Cuatrecasas et al., *Methods in Enzymology,* vol. 31, page 345 (1969), etc.), or physically (in a manner as described in, e.g., K. Kato et al., *J. Biochem.,* vol. 82, page 261 (1977), etc.); or one can impregnate porous materials containing fine particles with an aqueous solution containing the protein described above followed by freeze drying. The freeze drying can be conducted in a conventional manner, e.g., by evacuating a freeze dried material under reduced pressure of about $10^{-2}$ to about $10^{-4}$ mm Hg to sublimation. Details of freeze drying and its conditions, etc. are described in *Methods in Enzymology,* vol. 22, page 33 (1971), published by Academic Press, New York (1971).

Because of its excellent water-retention property, the porous material described above retains the required amount (at least 2 μl) of spotted or dropped sample liquid for a time period sufficient for the immune reaction to proceed. To exhibit this water-retention or absorbing capability of the porous material more effectively, it is preferred that the reaction layer composed of the porous material have an area smaller than that of the detection element which is optionally provided on the reaction layer.

The term "detection element" as used herein refers to a detection layer for receiving detectable signals released or formed in the element and, in the case that auxiliary layers for assisting the function of the detection layer in addition to the detection layer are present, collectively refers to the detection layer plus the auxiliary layers.

It is preferred that the reaction layer be superimposed on the detection layer so as to not extend over or project over the edges of the detection element, which should ensure an area enabling appropriate optical measurement as a final result. In such a multilayer analysis element, when a sample liquid is spotted or dropped thereon, undesired swelling of the reaction layer in the horizontal direction is only slightly observed, rather the reaction layer swells only so as to increase the thickness thereof.

Accordingly, the multilayer analysis element can retain a sample liquid in the reaction layer for a time period sufficient for the immunologically competitive reaction to proceed, which results in a greater change of the signal amount. In addition, curling (which is observed with conventional multilayer analysis films) does not occur; such is particularly advantageous in optical measurement.

The reaction layer can contain, in addition to an antibody, various reagents necessary for the specific protein-binding reaction and reactions which enable detection, except for labelled substances (e.g., a labelled antigen) which is incorporated in the detection layer.

Incorporation of the labelled antigen into the reaction layer should be avoided since the measurement sensitivity of an analyte is seriously decreased. Further, the reaction layer can be composed of two or more layers; for example, a sample liquid can be sequentially exposed to two separate specific protein-binding reactions by incorporating different compositions into each of the two layers so that a detectable signal, if it is weak, can be intensified. In this case, a specific binding protein (antibody, etc.) for interfering components in a sample liquid can be incorporated in the upper layer and the interfering components thereby eliminated. Thereafter, an antigen-antibody reaction in which the analyte is used as a second antigen or antibody can be effected in the lower reaction layer.

In a preferred embodiment of this invention, the reaction layer is provided on the detection layer, directly or directly via various functional layers such as a timing layer for controlling a rate of a liquid to be transported from the reaction layer, a light reflection layer or light absorption layer, etc.

The reaction layer, which is designed to have an area smaller than that of the detection layer in one embodiment of this invention, is of significance in that the reaction layer is physically restricted from expanding in the horizontal direction. Accordingly, it is difficult to specify the area thereof with a specific numerical range; rather, the area is determined depending upon or taking into account the necessary amount of sample liquid spotted or dropped, the kind and concentration of specific component, etc. and production cost.

It is necessary that the detection element have or exhibit planarity upon measurement in order to maintain accuracy of measurement; accordingly, it is generally necessary for the detection element to comprise supporting means, such as a frame, for mechanically compressing the element at the edge portions. On the other hand, it is sufficient that the reaction layer have an area sufficient to cover openings for spotting or dropping liquid therethrough. If the reaction layer is extended to the supporting means provided at the edge portions of the detection layer, i.e., if the reaction layer has the same area as that of the detection layer, such would result in waste of expensive reagents.

A protein which specifically recognizes and binds to an analyte or specific component is incorporated into the reaction layer. The content of the specific protein to be incorporated in the reaction layer is, of course, determined depending upon the concentration of an analyte, generally in the range of from about 1/1000 to about 100 times, preferably 1/100 to 100 times the concentration of the analyte.

Representative methods for incorporation include:

(1) impregnating a fibrous and/or non-fibrous, porous material with an aqueous medium containing the protein and then freeze drying in a conventional manner;

(2) linking an amino group or a carboxyl group of immunoglobulin to a fibrous and/or non-fibrous, porous material directly or indirectly through a linking component;

(3) in the case of adding fine particles, adding the fine particles after binding the protein to the fine particles through covalent binding or adsorption or through a linking component such as an Fc fragment complex, and so on.

The protein contained in the reaction layer exhibits a specific binding capability in an aqueous medium only when a predetermined volume of a sample liquid is spotted or dropped thereon.

Accordingly, of the above methods, physical adsorption or the method impregnating a porous material with a protein-containing liquid and then simply freeze drying the same—resulting in a state where the protein remains mixed—are preferred as compared to the method in which the protein is immobilized by, e.g., covalent linking, etc., since inactivation upon dropping of a sample liquid is minimized and binding capability is rapidly exhibited.

The protein capable of specifically binding a specific component (analyte) to be measured is determined depending upon the analyte.

The specific component (analyte) measured using the multilayer analysis element of this invention refers to a component having antigenicity (potential of an antigen to combine with its specific antibody) or an antibody, present in a liquid containing a biological component or body fluids such as blood, serum, spinal fluid, saliva, etc.

Representative examples of analytes are given below:

(I) Polypeptides, proteins, polysaccharides, nucliec acids and complexes thereof Complexes are bacilla, viruses, cell membranes, genes, nuclei, etc. The molecular weight of these complexes is at least 5,000, ordinarily 10,000 or more. Polypeptides and proteins generally have a molecular weight of from 5,000 to 5,000,000, usually 20,000 to 1,000,000. In the case of peptide hormones the molecular weight thereof generally ranges from 5,000 to 60,000.

(a) Proteins (1) Simple Proteins:

protamine, albumin, globulins ($\alpha$, $\beta$, particularly immunoglobulin, IgG, IgA, IgE, IgM, IgD), scleroproteins (structural proteins such as collagen, elastin, actin, etc.);

(2) Conjugated Proteins:

mucoprotein, chromoprotein, lipoprotein, nucleoprotein, glycoprotein, phosphoprotein;

(3) Other Proteins Including Enzymes and Complements:

(b) Peptide Hormones insulin, glucagon, somatotropin, corticotropin, gonadotropin, gastrin, secretin, pituitary hormone, etc., precursors thereof and metabolites thereof;

(c) Microoraganism-Originated Antigenic Polysaccharides coccus (Streptococcus, Staphylococcus, etc.), bacillus bacillus anthracis, bacillus subtilis, clostridium tetani, etc.), actinomyces (actinomyces, etc.), eumycetes (nocardia, aspergillus, candida, etc.), rickettsia (typhus, tutgamushi disease, Rocky Mountain spotted fever, Q-fever, etc.), viruses (herpes, adenoid vegitation, albo, hepatitis, etc.), spirochaeta (syphilis, leptospira, treponema, etc.) and other pathogenic bacteria;

(II) Antigenic Low Molecular Weight Materials

Antigenic low molecular weight materials have a molecular weight of generally from 100 to 2,000, usually 125 to 1,000, e.g., drugs, agricultural chemicals, small peptides, amino acids, low molecular weight hormones and metabolites thereof.

(a) Drugs alkaloids (morphine, codeine, kinine, digoxine, etc.), 5- or 6-membered lactams (barbiturate, etc.), aminoalkyl benzenes (amphetamine, epinephrine, catecholamine, etc.), benzo-heterocyclic compounds (oxazepam, chloropromazine, etc.), purines (theophylline, caffeine, etc.), vitamins (A, B complex, C, D, E, etc.), prostaglandins, antibiotics (penicillin, tetracycline, cephalosporin, etc.), amino-glycosides (gentamycine, kanamycine, etc.), other drugs (methadone, meprobamate, lidocaine, griseoflavine, etc.), and metabolites of these drugs.

(b) Agricultural Chemicals halogenated biphenyls, phosphoric acid esters, thiophosphate, etc. and metabolites thereof.

(c) Others small peptides, amino acids, low molecular weight hormones, triiodothyronine, thyroxine, encepharine, bradykinine, angiotensine I and II, and metabolites thereof.

Analysis of an analyte causing enzyme immunoassay reactions of the homogenous type is based upon the principle that labelled and unlabelled specific components competitively react with a protein which specifically binds these specific components to thereby cause a change in enzyme activity producing a signal enzyme (including its precursor) and, as a result, cause a change in the amount of the signal produced. In this invention, the amount of change (i.e., modulated amount) of the thus modulated signal is measured.

Typical examples of labels that enable one to analyze an analyte based upon such principle include enzymes, enzyme inhibitors, coenzymes, combination of substrates and secondary enzymes, allosteric effectors, etc.

In this invention, spectrophotometry, fluorophotometry, or the like can be utilized as the optical measurement system. Optical measurement can be practiced by a reflection or transmission system, but a reflection system is preferred in the effect of interfering materials can be eliminated.

In spectrophotometry, ultraviolet rays, infrared rays, etc., can be utilized in addition to visible rays.

Fluorophotometry is effected with a fluorescent substance in the reaction layer, or, preferably, a fluorescent substance diffused into the detection layer, and the excitation light and fluorescence wavelength can be optionally chosen depending upon the purpose and utility desired.

Labelling of a specific component being analyzed is carried out in a conventional manner as described in, e.g., Avrameas et al., *Immunochemistry*, vol. 8, pages 1175 to 1179 (1971) using a glutaraldehyde cross linking technique; P. Nakane et al., *J. Histochem. Cytochem.*, vol. 22, pages 1084 to 1091 (1974) using a periodic acid cross linking technique; T. Kitagawa et al., *J. Biochem.*, vol. 79, pages 233 to 236 (1976) using a maleimide cross linking technique; D. Clyne et al., *J. Histochem. Cytochem.*, vol. 21, pages 233 to 240 (1973) using an isocyanate cross linking technique; T. Ternynck et al., *Immunochemistry*, vol. 14, pages 767 to 774 (1977) using a benzoquinone cross linking technique; U.S. Pat. No. 3,654,090 issued to A. H.W. M. Schuurs; B. F. Erlanger et al., *J. Biol. Chem.*, vol. 234, page 1090 (1959); *Methods in Enzymology*, vol. 22, page 33 (1971), published by Academic Press, New York, etc. Further, enzyme labelling can be effected by the methods described in the above citations and also per: Eiji Ishikawa et al., *Enzyme Immunoassay*, published by Igaku Shoin Publishing Co., Ltd. (1978); Wisdom, *Clin. Chem.*, vol. 22, page 1243 (1976); A. Voller et al., *The Enzyme Linked Immunosorbent Assay*, published by Flowing Publications, Guerney, Europe (1977); etc. Fluorescein labelling can be performed in a manner as described in *Series of Clinical Test Technique*, vol. 4, subtitled "Immunoserological Test", edited by Tadashi Kawai, published by Igaku Shoin Publishing Co., Ltd. (1977), pages 97 to 102.

In the case that substrates, inhibitors, prosthetic groups (coenzymes, etc.) or the like are employed as labels, labelling is performed in a manner similar to the case using enzymes. Labelling of labelled substances employed in the reaction of type (1) described above is described in Japanese Patent Application (OPI) Nos. 5491/73 and 20134/79; in the case of reactions of types (2) and (3) described above, in Japanese Patent Application (OPI) Nos. 105291/78 and 104896/80; and, in the case of the reaction of type (4), in Japanese Patent Application (OPI) No. 136896/79.

Representative examples of enzymes, substrates, inhibitors and prosthetic groups (coenzymes, etc.) which can be employed as labels in the respective reactions of types (1) to (4) described above are given below.

| (1)-1 Examples of enzymes as labels used in the reaction of Type (1): | |
|---|---|
| Hydrolase (also called carbohydrolase) | amylase, lactase, maltase sucrase, emulsin |
| Nuclease | polynucleotidase, nucleotidase |
| Aminase | alginase, urease, glutaminase, transaminase |
| Purine Deaminase | adenase, guanase |
| Peptidase | aminopolypeptidase, carboxypeptidase, dipeptidase, prolinase |
| Proteinase | pepsin, tripsin, catepsin, renin, chymotrypsin, papain, ficin |
| Esterase | lipase, esterase, phosphatase, sulfatase, chloinesterase, acetylcholinesterase |
| Iron Enzyme | catalase, cytochromeoxidase, peroxidase |
| Copper Enzyme | tyrosinase, ascorbic oxidase |
| Enzyme Containing Coenzyme I and/or II | alcohol dehydrogenase, malic dehydrogenase, isocitric dehydrogenase, lactic dehydrogenase, $\beta$-hydroxybutyric dehydrogenase, glucose dehydrogenase, Robison ester dehydrogenase, aldehyde dehydrogenase |
| Cytochrome Reduction Enzyme | succinic dehydrogenase |
| Yellow Enzyme | Haase enzyme, xanthine oxidase, D- or L- aminoacid oxidase, TPN-cytochrome AC reductase, DPN-cytochrome C reductase |
| Hydrolase | fumarase, aconitase, enolase |
| Mutase | glyoxalase |
| Desmolase | aldolase, carboxylase, $\beta$-ketocarboxylase, amino acid decarboxylase, carbonic anhydlase |
| Other Enzymes | phospholylase, phosphohexoisomerase, hexokinase, phosphoglucomutase |

Enzymes described above and other enzymes, enzyme sources, substrates, as well as final products which can be employed in this invention, are described in detail in *Practical Physiological Chemistry*, pages 306 and 307 (1954) published by McGrow Hill Co., Ltd. (New York), Perman's *Enzyme Handbook*, Springer Verlag Co., Ltd., New York (1969).

| (1)-2 Examples of enzymes and inhibitors used in combination with such enzymes for intensifying modulated signals used in the reaction of Type (1): | |
|---|---|
| Enzyme | Inhibitor |
| $\gamma$-cystathionase | 2-amino-4-pentenic acid (I) 2-amino-4-chloro-4-pentenic acid (II) 3,3-dichloroaniline (III) 3,3,3-trichloroaniline (IV) |
| Alanine Racemase | 3,3,3-trichloroaniline D-cycloserine |
| Tryptophanase | 3,3,3-trichloroaniline |
| Tryptophane synthetase ($\beta_2$ and $\alpha_2\beta_2$) | 3,3,3-trichloroaniline |
| Lactic Oxidase | 2-hydroxy-3-butenic acid |
| Monoamine oxidase | N,N,N—trimethyl-2-propenylamine |
| Plasma Amine Oxidase | 2-bromoethylamine 2-propenylamine 2-chloroallylamine phenylglycine p-nitrophenylglycine aminoacetonitrile |
| $\beta$-Cystathionase | 3,3,3-trichloroaniline 2-amino-3-hydroxypropyl-1 3'-carboxy-3'-amino-1'-propenyl-1 ether |
| Aspartic Aminotransferase | L-2-amino-4-methoxy-trans-3-butenic acid |
| $\gamma$-Aminobutyric Acid-$\alpha$-Ketoglutarate aminotransferase | Ethanolamine O—Sulfate |
| Formylglycinamide Ribonucleotide Amide Transferase | diazoxonorleucine diazoxonorvaline |
| Transpeptidase | $\Delta^3$-7-aminocephalosporic acid |
| B$_6$ Binding Enzyme | mimocine |
| Serine protease | fisostigmin |
| Glutamine Synthetase | methionine sulfoximine |

-continued

| Malic Dehydrogenase and Lactic Dehydrogenase | blue dextran |
| --- | --- |
| Peroxidase | o-dianisidine dextran |

(2)-1 Examples of inhibitors used in the reaction of Type (2) are shown in combination with examples of the enzymes whose enzyme activity is inhibited by the inhibitors:

| Inhibitor | Enzyme |
| --- | --- |
| Organic phorphoric acid Triesters | tryspin |
| Organic phosphonic acid Triesters | acetylcholinesterase |
| Organic phosphothioates | butylcholinesterase |
| | chymotrypsin |
| | thrombin |
| | elastase |
| | adenosine deaminase |
| Alkylsulfonates | acetylcoholinesterase |
| Alkyl Isocyanates | elastase |
| | trypsin |
| | chymotrypsin |
| p-Chloromercury Benzoate Derivative | papain |
| p-Chloromercury-benzoate derivative | alcohol dehydrogenase |
| | chymopapain |
| | clostridiopeptidase B |
| | adenosine deaminase |
| | lipase |
| | β-amylase |
| | pepsin |
| | glyceroaldehyde-3-phosphoric dehydrogenase |
| | alanineaminotransferase |
| | hexokinase |
| Substrate Epoxy Compound | pepsin |
| 6-Diazo-5-oxo-L-norleucine Derivative | glutaminase |
| Iodoacetic Acid Derivative | acid deoxyribonuclease II |
| | alcohol dehydrogenase |
| N—Bromosuccinimide Derivative | acid deoxyribonuclease II |
| | dextranase |

Of the above inhibitors, particularly preferred inhibitors are compounds containing therein an organic phosphoric group represented by the formula:

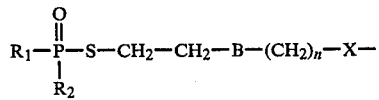

wherein $R_1$ and $R_2$ each represents an alkyl group or an alkoxy group having 1 to 10 carbon atoms; B represents a divalent group such as —O—, —CO—, —S—, —NH—, —CONH—, —CH=CH—, —C≡C—, a phenylase group, a sulfonium and ammonium salt, etc.; n represents an integer of from 1 to 10 and X represents a functional group such as hydroxy, amino, carboxy, α-halomethoxycarboxy, etc.

Further, compounds containing therein a group represented by the formula:

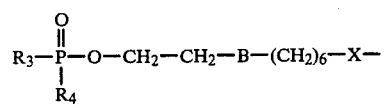

wherein $R_3$ represents the same meaning as defined for $R_1$ and $R^2$ above; $R_4$ represents an organic splitting-off group (e.g., p-nitrophenyl, hydroxyquinolyl, etc.); B and X have the same meanings as defined above, are also particularly preferred as inhibitors.

When acetylcholinesterase which is preferably used in this invention is used, inhibitors represented by the formula are preferably used:

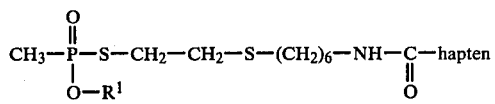

wherein $R^1$ represents ethyl or n-butyl.

(2)-2 Examples of inhibitors used in the reaction of Type (2) are shown in combination with examples of the enzymes whose enzyme activity is inhibited by the inhibitors.

| Inhibitor | Enzyme |
| --- | --- |
| Acetazolamide | carbonic anhydrase |
| Sulfanilamide | carbonic anhydrase |
| Phenyltrimethyl ammonium ion | acetylcholinesterase |
| Saccharo-1,4-lactone | β-glucuronidase |
| 4-Amino-10-methylbutyroyl-gultamic acid | dihydrophorate reductase |

An example of a preferred inhibitor is:

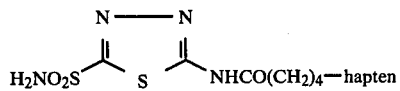

(3)-1 Examples of prosthetic groups used in the reaction of Type (3) described above (examples of apo enzymes are also shown along with the prosthetic groups used in combination therewith).

| Prosthetic Group | Apo Enzyme |
| --- | --- |
| FAD | glutathione reductase |
| FMN | cytochrome reductase |
| FMN | NADPH |
| FAD | glucose oxidase |
| FAD | lipoamide dehydrogenase |
| Heme | peroxidase |
| Heme | cytochrome C | wherein:
FMN: flavin mononucleotide
FAD: flavin adenine dinucleotide

Details on prosthetic groups and apo enzymes used in combination therewith are described in Scott et al., *J. Biol. Chem.* vol. 238, page 3928 (1963), Haas et al., ibid., vol. 143, page 341 (1942), Stahl et al., *Biochimica Physica Acta*, vol. 185, page 39 (1969), Bisel et al., ibid., vol. 206, page 224 (1970), etc.

(3)-2 Examples of allosteric effectors used in the reaction of Type (3) are shown along with examples of enzymes, whose enzyme activity is changed or modulated by the allosteric effector, wherein (+) indicates a positive allosteric effect and (−) indicates a negative allosteric effect.

| Allosteric Effector | Enzyme |
| --- | --- |
| L-Isoleucine (−) | biosynthesis L-threonine |
| L-Valine (+) | deaminase |
| CTP (-31 ) | aspartate transcarbamylase |
| ATP (+) | |
| dTTP (−) | deoxycytidilate aminohydrolase |
| dCTP (+) | |
| ATP (−) | phosphofructokinase |
| 3',5'-AMP (+) | |
| dTTP (−) | deoxythymidinekinase |
| dCDP (+) | |
| α-ketoglutarate (−) | NAD-isocitric dehydragenase (N. Crassa) |

(3)-2 Examples of allosteric effectors used in the reaction of Type (3) are shown along with examples of enzymes, whose enzyme activity is changed or modulated by the allosteric effector, wherein (+) indicates a positive allosteric effect and (−) indicates a negative allosteric effect.

| Allosteric Effector | Enzyme |
|---|---|
| Citric acid (+) | |
| 5'-AMP (+) | NAD-isocitric dehydrogenase (yeast) |
| L-Threonine (−) | homoserinedehydrogenase |
| L-Leucine (+) | |
| L-Methionine (+) | |
| ADP (+) | L-threoninedeaminase |
| L-Valine (−) | acetolactate synthetase |
| L-Threonine (−) | thoreonine aspartokinase |
| UDP-N—acetylglucos-amine (−) | L-glutamine-D-fructose-6-phosphate transaminase |
| Glucose-6-phosphate (+) | glycogen synthetase |
| ATP (−) | glutamate dehydrogenase |
| GTP (−) | phosphorylase |
| Reductive NAD (−) | |
| Estrogen (−) | |
| Thyroxine (−) | |
| ADP (+) | |
| Leucine (+) | |
| Methionine (+) | |
| ATP (−) | |
| 5'-AMP (+) | |
| CMP-N—acetyl-neuramic acid (−) | UDP-N—acetylglucosamine-2-epimerase |
| L-Threonine (−) | homoserine dehydrogenase |
| L-Lysine (−) | lysine aspartokinase |
| 5'-AMP (−) | fluctose-1,6-diphosphatase |

Details are given in *Journal of Molecular Biology*, vol. 12, page 88 (1965).

(4)-1 Examples of combinations of reagents used in the reaction of Type (4) described above; that is, examples of combinations in which a first enzyme shown at Column 4A changes or modulates the local concentration of a compound shown at Column 4B and, in proportion thereto, the relative activity of a second enzyme or a label for producing a signal as shown at Column 4C:

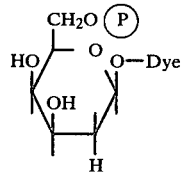

| First Enzyme (4A) | Compound (4B) | Second Enzyme or label Forming Signal (4C) |
|---|---|---|
| phosphoglucose isomerase | G-6-P | G-6-P dehydrogenase |
| Alkali phosphatase | (sugar-phosphate-dye structure) | β-galactosidase |
| NAD-dependent dehydrogenase (IUB Class 1.1.1) | NADH | phenazine metosulfate or Meldra blue |
| Glucose oxidase | H₂O₂ | horse radish peroxidase |
| β-Galactosidase | tridecanal | bacterial luciferase |
| Maleate dehydrogenase | phenazine metosulfate | β-galactosidase |

| First Enzyme (4A) | Compound (4B) | Second Enzyme or label Forming Signal (4C) |
|---|---|---|
| Horse radish peroxidase | O—O / HO—(phenol) | Br-anthracene-Br |
| | O₂N—(phenyl)—OCO / NO₂ with O=...=O | fluorescin |
| Alkali phosphatase | G-6-P | G-6-P dehydrogenase |
| Triose phosphate isomerase | HOCH₂COCH₂O(P) | α-glycerophosphate dehydrogenase |
| Alkali phosphatase | G-6-P | G-6-P dehydrogenase |
| Hexokinase | | G-6-P dehydrogenase |
| Phosphoglucomutase | " | G-6-P dehydrogenase |
| Pyruvate kinase | pyruvate | lactate dehydrogenase |
| β-Galactosidase | fluorescin | umbelliferone |
| " | " | horse radish peroxidase |

Of the above enzymes employed as labels, peroxidase, β-galactosidase, glucose-6-phosphate dehydrogenase, acetylcholinesterase, alkali phosphatase and glucose oxidase, are particularly advantageously employed in this invention.

The detection layer which is advantageously provided beneath the reaction layer in the analysis film in accordance with this invention receives a signal modulated through a competitive reaction, i.e., reaction products or a detectable signal released or formed in the reaction layer as a result of the competitive reaction.

The detection layer is basically located below the reaction layer since it receives the detectable signal that is produced in or released from the reaction layer.

The detection layer can be composed of the same fibrous and/or non-fibrous porous materials as is used for the reaction layer, e.g., textiles, non-woven fabrics, paper, etc.

Hydrophilic high molecular weight substances can be employed as binders for the reaction layer as well as for the detection layer.

Examples of binders which can be employed in the reaction and detection layers per this invention include natural hydrophilic high molecular weight substances such as gelatin, agarose, sodium alginate, carboxymethyl cellulose, methyl cellulose, etc.; hydrophilic synthetic high molecular weight substances such as polyacrylamide, polyvinyl alcohol, polyvinylpyrrolidone, sodium polyacrylate, polyhydroxyethyl methacrylate, etc.

In the case that a labelled specific component has a molecular weight of several hundred thousands e.g., IgG, then agarose, polyacrylamide, sodium polyacrylate and copolymers containing acrylic acid are particularly preferred since macromolecular substances such as IgG can be appropriately retained in the network formed by these binder materials.

Incorporation of water-absorbing polymers into the detection layer is preferred since a signal can more effectively be collected in the detection layer, whereby sensitivity as well as metering capability are improved. Further, when a layer into which a water-absorbing polymer is incorporated is provided above, below or adjacent the detection layer, a resulting signal is more effectively collected and such is advantageous. As such water-absorbing polymers, hydrophilic synthetic or natural high molecular weight substances as described above can be employed singly or as a combination of two or more thereof. The use of gelatin in combination with polymers having a carboxy group, e.g., vinylpyrrolidone-acrylic acid copolymers, renders swelling extremely easy and gives particularly preferred results.

In general, materials which provide capability of absorbing water of at least 5 times their dead weight, preferably at least 10 times, in 5 minutes, are preferred for use in the water-absorbing layer.

The reaction layer is provided on the detection layer, directly or indirectly via various functional layers such as a light-reflection or light-shielding layer, an adhesive layer, etc.

A reagent layer can also be provided, if desired or necessary, above or below the reaction layer; however, taking the function of the reagent layer into account, it is preferred that the reagent layer usually be located over the reaction layer.

The reagent layer can contain a variety of reagents essential or desirable to effect a competitive reaction and other reactions which render detection and optical measurement of the formed signal possible, except for an antibody. For example, enzymes described above; enzyme substrates; coenzymes described above, e.g., NAD, NADH, NADP, NADPH, etc.; buffers for maintaining pH constant; surface active agents; gelatin; stabilizers for bovine serum, albumin, etc.; can be persent. In addition, blockers can also be incorporated into the reagent layer to make a conjugated analyte free, the analyte being conjugated with a body component such as protein (e.g., salicylic acid, 8-anilino-1-naphthalense-sulfonic acid, etc. for measurement of $T_4$).

A part of these reagents can also be incorporated into a spreading layer and/or spreading-assisting layer, if desired or necessary, which can be provided above the reagent layer. Further, a part of these reagents (e.g., blocker reagents) can previously be mixed with a sample solution without incorporating the same into the analysis film and the resulting mixture can then be dropped or spotted onto the analysis film.

It is often preferred that a timing layer be provided between the reaction layer and the detection layer. The timing layer exhibits a function such that a sample liquid can be retained in the reaction layer for a certain period of time to thereby complete competitive reaction and then allows the resulting reaction product to diffuse into the detection layer. When this layer is provided, detection sensitivity and quantitative nature are further markedly improved. As materials for the timing layer, the aforesaid hydrophilic synthetic or natural polymers can be employed singly or in combination of two or more. Gelatin having various degrees of hardness is preferably used in the timing layer depending upon the purpose; strongly hardened gelatin can delay the rate of transporting a sample liquid and relatively mildly hardened gelatin can provide a mild degree of slowing the rate of transportation of a liquid.

In addition to the above, various other functional supporting layers or structural auxiliary layers (some of which have already been mentioned above) conventional in the art can be provided in the analysis film of this invention for purposes of supporting the basic functions of the reaction layer or maintaining the structure thereof.

These supporting or auxiliary layers include a timing layer to retain a sample liquid in the reaction layer for a certain period of time thereby some of reactions being delayed, a spreading (or diffusing) layer to assist metering and spreading of a sample liquid and a hematocyte separating layer (hematocytes interfere with optical measurement of a detectable signal in certain analyse and is separated using a material which retains macromolecular hematocytes therein) or an adhesive layer, a support for physically supporting the reaction layer, a light-shielding layer for effecting optical measurement, a water-absorbing layer for further enhancing water absorption, etc., all of which are optional. Details of these supporting or auxiliary layers are described in, e.g., U.S. Pat. No. 4,292,272.

The location of these auxiliary layers can easily be determined by one skilled in the art depending upon the functions thereof and it is believed to be unnecessary to provide detailed descriptions thereon herein.

The ayer thicknesses of essential and various optional function-supporting layers included in the analysis film of this invention can vary depending upon kind of layer structure, functions required depending upon the analyte, etc., but the following layer thickness as are generally desired for each of the layers:

| | |
|---|---|
| reaction layer: | 50 μm to 2 mm, preferably 200 μm to 1 mm |
| detection layer: | 3 to 200 μm, preferably 5 to 50 mm |
| support: | 50 μm to 2 mm, preferably 100 to 500 μm |
| reagent layer: | 50 μm to 2 mm, preferably 100 to 500 μm |
| spreading layer: | 50 to 500 μm |
| light-shielding layer: | 1 to 50 μm, preferably 2 to 20 μm |
| water-absorbing layer: | 3 to 200 μm, preferably 5 to 50 μm |
| timing layer | 2 to 50 μm |

In a preferred embodiment of this invention, a light-shielding layer, which permits effective passage of radiation used to detect a modulated signal produced in the analysis film, is provided between the reaction layer and the detection layer; it is preferred that the light-shielding layer be a radiation absorbing layer or reflecting layer.

A radiation absorbing layer is effective to absorb excitation irradiation to minimize a blank value due to reflection of the excitation wavelength, for example, when measurement of reflecting fluorescence is performed from the support side. The design of a suitable system dependent on the excitation wavelength and the emission wavelength will be apparent to one skilled in the art. Various dyes, coloring agents, pigments, etc., can be employed in addition to yellow colloidal silver.

On the other hand, a radiation reflecting layer is used in the case of measuring reflected spectral absorption from the support side and is obtained by dispersing a white powder, such as finely divided $TiO_2$, $BaSO_4$, etc., in a hydrophilic high molecular weight binder in an amount of 1 to 25 wt% and forming a layer from the dispersion in a thickness as described above.

It is preferred that a labelled compound or a detectable signal which renders detection of a specific component possible be effectively collected in the detection layer. For this reason, materials having particularly excellent water-absorbing capability among the above described materials, e.g., hydrophilic natural or synthetic high molecular weight substances such as gelatin, polyvinyl alcohol, etc., are preferably employed for the detection layer. In addition, a filter paper, a glass fiber filter paper, a micro filter, etc. an also be employed.

Further, in another preferred embodiment of this invention, substances having a strong interaction with a labeled compound or reaction product which permits detection, e.g., mordanting agents, are preferably incorporated into the detection layer in order to collect the compound or reaction product therein. As such mordanting agents cationic polymers as described in Japenese Patent Application (OPI) No. 24694/80, e.g., quaternary salts of 4-vinylpyridine and 2-methyl-1-vinylimidazole, N,N,N-trimethyl-N-vinylbenzyl ammonium chloride, etc.; other cationic polymers well known in the photographic art; and anionic polymers as described in Japanese Patent Application No. 28158/81 can be used. Latexes of these polymers are preferred in view of improved diffusion resistance, ease in handling, etc.

To improve various efficiencies such as coating efficiency, diffusibility of diffusible compounds, reactivity, preservability, etc., various additives such as surface active agents, pH controlling agents, finely divided powders, antioxidants, other organic or inorganic additives can also be incorporated in the detection layer.

Supports used for the analylsis film of this invention are transparent to optical measurement and it is generally preferred that the supports be water impermeable. Specific examples of light transmitting water impermable supports include plastic films such as polyethylene terephthalate, cellulose esters (cellulose diacetate, cellulose triacetate, cellulose acetate propionate, etc.), polycarbonate, polystyrene, polymethyl methacrylate, etc., and a glass plate. Known transparent supports having a thickness as described above can be used.

As supports for an analysis film in which a specific component labelled with a fluorescent substance is employed., low fluorescence radiation transmitting supports such as polycarbonate, cellulose esters, polystyrene, etc. are particularly advantageously employed.

In the case that a support is hydrophobic and provides poor adhesion to the hydrophilic binder in the detection layer, conventional auxiliary treatments such as to render the surface of the support hydrophilic (e.g., ultraviolet irradiation, electron irradiation, flame treatment, hydrolysis with an alkali, plasma treatment, glow discharge treatment, etc.), provision of a subbing layer comprising an appropriate adhesive for the hydrophilic binder in both the support and the detection layer on the surface of the support, formation of minute uneven portions (brushing, electrolytic etching, etc.) on the surface of the support to a degree that light transmittance is not significantly decreased, ect. can be performed.

A sample liquid-spreading layer (hereafter simply referred to as a spreading layer) can also be provided, if desired or necessary, as the uppermost layer of the analysis film of this invention. The spreading layer has the effect of uniformly spreading a sample liquid dropped onto the analysis film. In the case that the reaction layer is composed of a woven fabric, nonwoven fabric or paper, the spreading layer will not generally be used, of course.

For the spreading layer, fabrics which have been rendered hydrophilic are employed. As such fabrics rendered hydrophilic, there are fabrics that have been cleaned and rinsed with water to defat the same followed by drying and fabrics that are, after cleaning and rinsing with water to defat the same, impregnated with a small amount of a surface active agent, a wetting agent, a hydrophilic polymer or a dispersion of finely divided powders of $TiO_2$ or $BaSO_4$ in a hydrophylic polymer. Techniques using fabrics which have been subjected to hydrophilic treatment as the spreading layer, kind of fabrics, layer thickness, etc., are described in detail in Japanese Patent Application (OPI) No. 154356/80, U.S. Pat. No. 4,292,272, etc., and the some can be applied to this invention in accordance with the description therein.

To perform analysis using the analysis film in accordance with this invention, a sample liquid is dropped or spotted on the analysis film followed by incubation for generally 1 minute to 24 hours (which varies depending upon an analyte, mode of reaction, layer structure, etc.), preferably at temperatures ranging from 0° to 65° C., more preferably 10° to 45° C.

Preferred embodiments of this invention include:

1. In the analysis film of this invention and a method for analysis using the same:

(1) A detectable signal is absorption of light in the ultraviolet or visible region.

(2) A detectable signal is an emission generated by absorption of light in the ultraviolet or visible region.

(3) A detectable signal is emission in the ultraviolet or visible region.

(4) A protein specifically binding an analyte is contained in the reaction layer in a state where the protein is not chemically bound to a fibrous and/or non-fibrous porous material.

2. In a method for analysis using a multilayer analysis film comprising a reaction layer, a light-shielding layer and a detection layer through spectrophotometric measurement of a changed signal, the light-shielding layer is a light-reflection layer.

3. In a method for analysis using a multilayer analysis film comprising a reaction layer, a light-shielding layer and a detection layer through fluorometric measurement of a changed signal, the light-shielding layer is a layer which absorbs excitation light and/or emitted fluoescence.

Hereafter this invention will be described in more detail with reference to the examples below.

EXAMPLE 1

(1-1): Synthesis of N-methyl-N-carboxymethylglycylthyroxine methyl ester (T$_4$-MEMIDA)

In 15 ml of dimethylformamide (DMF), 2 g of thyroxine methyl ester hydrochloride was dissolved and 500 μl of triethylamine was added to the resulting solution. After 10 minutes passed, a solution of 0.55 g of N-methyliminodiacetic acid anhydride in 5 ml of tetrahydrofuran (THF) was added to the mixture. After completion of the reacton, the reaction mixture was condensed using a rotary evaporator and the residue was dissolved in 50 ml of THF. Further, 150 ml of ethyl acetate was added to the solution. After stirring the mixture by shaking, the ethyl acetate layer was taken out and washed three times with distilled water and then once with a saturated aqueous sodium chloride solution. After the ethyl acetate layer was dried over anhydrous sodium sulfate, the supernatant was condensed using a rotary evaporator. To the residue, 20 ml of THF was added and then a small quantity of n-hexane was added to form precipitates. The precipitates were subjected to suction filtration to obtain white crystals. The crystals were dried in a dessicator under reduced pressure to obtain 2.3 g of white crystals. The yield was 69%.

(1-2) Synthesis of thyroxine-bound malic dehydrogenase ($T_4$-MDH)

In 200 μl of DMF, 10 mg of $T_4$-MEMIDA obtained in (1-1) above was dissolved and 1.5 mg of N-hydroxysuccinic imide was added to the resulting solution. Under ice cooling, 2.5 mg of 1-ethyl-3-(3-dimethylaminopropyl)carbodiimide (ECDI) was added and the resulting mixture was reacted at 4° C. overnight to obtain an active ester solution.

Separately, 25 mg of malic dehydrogenase (MDH) derived from mitrochondria of pig heart muscle, manufactured by Boehringer Mannheim Co., Ltd.) was dissolved in 5 ml of 0.05M sodium carbonate buffer solution (pH 9.2). Under ice cooling, the active ester solution obtained above was added to the solution at a rate of 10 μl/min. After completion of the addition, the reaction mixture was stirred for 2 hrs. Then, the reaction mixture was subjected to gel filtration using Sephadex G-50 to obtain a fraction of MDH. This fraction showed 10 to 20% enzyme activity as compared to the initial MDH.

(1-3) Preparation of anti-thyroxine antibody

Into 20 ml of a 0.05M carbonate buffer (pH 9.0) containing 100 mg of bovine serum albumin (Fraction V, manufactured by Miles Labs., Co., Ltd.), 100 mg of $T_4$-MEMIDA activated in a manner similar to Example (1-2) was dropwise added and the mixture was reacted. The thus obtained reaction mixture was subjected to dialysis against the same buffer for 48 hrs. (2 liters×4 times) to eliminate unreacted matter and to distilled water for 48 hrs. (2 liters×4 times) to desalt the same. Thereafter, the desalted reaction product was freeze dried to obtain about 130 mg of dry solid.

It was confirmed that approximately 20 haptens were introduced per one molecule of bovine serum albumin. Using the thus obtained anti-thyroxine antibody, rabbits were immunized in a conventional manner to obtain $T_4$ anti-serum.

(1-4) Preparation of multilayer analysis film for detecting thyroxine

Onto a colorless transparent cellulose triacetate film (dry thickness, 130 μm), the layers described below were coated or laminated to prepare a multilayer analysis film:

(1) Water-absorbing layer:

A 5% aqueous gelatin solution was mixed with a copolymer of vinylpyrrolidone: acrylic acid=(9:1 wt.) in a ratio of gelatin to compolymer of 10:1 wt. and the mixture was coated on the cellulose triacetate film. The coated layer was dried at 35° C. for 10 minutes. The gelatin content after coating was 22.8 g/m² and the copolymer content was 2.8 g/m². Layer thickness was 19 μm.

(2) Detection layer:

A 5% aqueous gelatin solution and a copolymer of styrene and N,N,N-trimethyl-N-vinylbenzyl ammonium chloride as a mordant were coated in an amount of 3.02 g/m², respectively, and then dried at 35° C. for 10 minutes to form a detection layer. Layer thickness was 5 μm.

(3) Light-shielding layer:

A 6% aqueous gelatin solution containing yellow silver colloid was coated on the detection layer in an amount of 3.0 g/m² as silver. Layer thickness was 5 μm.

(4) Reaction layer:

The anti-$T_4$ serum prepared in Example (1-3) which had previously been diluted with a 0.02M sodium phosphate buffer (pH 5.5) containing 0.5% bovine serum albumin (BSA) was mixed with an aqueous solution of oxidative β-nicotinamide adenine dinucleotide (β-NAD). A glass fiber filter paper (TOYO Filter Paper GA-100, manufactured by Toyo Filter Paper Co., Ltd., void volume ca. 95%) having a thickness of 0.3 mm was cut into 1 cm squares and impregnated with the resulting mixture followed by freeze drying ($10^{-3}$ mmHg (about −20 to about −40° C.). The freeze dried material was put on the detection layer described above at the center thereof, which detection layer had been cut into 2 cm squares and the surface of which had been wet with water.

(5) Reagent layer:

The same glass fiber filter paper as used in the reaction layer was cut into 1 cm squares and impregnated with a mixture of $T_4$-MDH prepared in Example (1-2) and a glycinehydrochloride buffer (pH 5.2) containing 0.5% of a 0.1M aqueous sodium maleate solution. The mixture was contained in an amount of 70 μl per 1 square cm of the glass fiber filter paper. Thereafter, the material was freeze dried and laminated on the reaction layer.

Figure 6:
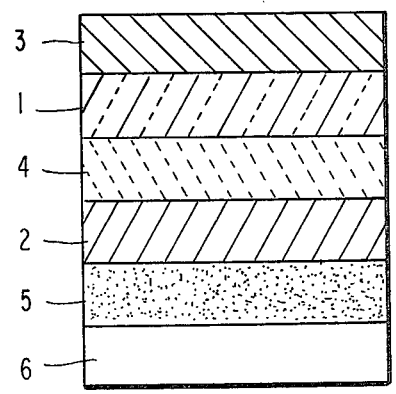

The layer structure of the thus obtained multilayer analysis film is shown in FIG. 6 wherein 1: reaction layer, 2: detection layer, 3: reagent layer, 4: light shielding layer, 5: water absorbing layer and 6: support.

(1-5) Preparation of calibration curve using standard thyroxine solutions

Onto the multilayer analysis film prepared in Example (1-3), 140 μl of standard solutions of thyroxine (manufactured by Sigma Co., Ltd.) in 0.05M phosphate buffered saline: PBS (pH 7.3) with thyroxine contents of from 1 to 20 μg/dl were dropped, respectively. After incubation at 37° C. for 15 minutes, fluorescence was measured from the support side (excitation wavelength, 340 nm; fluorescence wavelength, 460 nm). The results are shown in Table 1 below.

TABLE 1

| $T_4$ Content (μg/dl) | 1.0 | 2.0 | 4.0 | 8.0 | 14 | 20 |
|---|---|---|---|---|---|---|
| Relative Intensity of Fluorescence | 100 | 95 | 83 | 70 | 47 | 35 |

As is seen the results showed a quantitative response between the $T_4$ content and the relative intensity of fluorescence.

(1-6) Recovery Rate

To human serum with a thyroxine content of 7.6 μg/dl, a solution of standard $T_4$ in 0.05M of PBS (pH 7.3) was added to prepare samples containing $T_4$ in an amount of 1, 2, 4 and 8 μg/dl each, greater than the $T_4$ content present in original serum (prior to the addition of standard $T_4$). From each of the samples, 100 μl was taken and 100 μl of a 0.1N NaOH aqueous solution was added thereto. After allowing the mixtures to stand at room temperature for 10 minutes, 140 μl of mixture was dropped onto the multilayer analysis film prepared in Example (1-4) followed by incubation at 37° C. for 15 minutes. In a manner similar to Example (1-5), the relative intensity of fluorescence was determined.

The results obtained are shown in Table 2 below.

TABLE 2

| $T_4$ Added (a μg/dl) | Found Value (b μg/dl) | Calcd. Value (c μg/dl) | Recovery Rate (b/c × 100%) |
|---|---|---|---|
| 0 | 7.6 | 7.6 | — |
| 1.0 | 8.5 | 8.6 | 98.8 |
| 2.0 | 9.4 | 9.6 | 97.9 |
| 4.0 | 12.3 | 11.6 | 106 |
| 8.0 | 14.9 | 15.6 | 95.5 |
| | | | 99.6 average |

In the above table, numerical values were obtained with reference to the calibration curve obtained in Example (1-5).

EXAMPLE 2

A multilayer analysis film having the following layer structure was prepared in a manner similar to Example (1-4).

(1) Water absorbing layer:
same as in Example (1-4)

(2) Detection layer:
A mixture of a 5% aqueous gelatin solution with a 10% aqeuous 2,4dichloroindophenol phenazine metosulfate (PMS) solution and 3,3'-(4,4'-biphenylene)-bis(2,5-diphenyl-2H-tetrazolium chloride) (NeO-TB) was coated on the water absorbing layer in amounts of 3.02 g of gelatin, 0.37 g of PMS and 0.8 g of NeO-TB, respectively, per 1 m². Further, 3.0 g/m² of a copolymer of styrene and N,N,N-trimethyl-N-vinylbenzyl ammonium chloride was also coated as a mordant. Layer thickness was 6.0 μm.

(3) Reaction Layer:
same as in Example (1-4)

(4) Reagent layer:
same as in Example (1-4)

Using the thus prepared multilayer analysis film, the procedure as described in Example (1-5) was repeated. Reflection density was measured from the support side at 505 nm. Quantitative results as shown in Table 3 below were obtained.

TABLE 3

| Thyroxine Content (μg/dl) | 1.0 | 2.0 | 4.0 | 8.0 | 16 | 20 |
|---|---|---|---|---|---|---|
| Reflection Density | 1.21 | 1.15 | 1.02 | 0.89 | 0.60 | 0.55 |

(3-1) Binding of p-aminolidocaine hemisuccinamide and glucose-6-phosphodehydrogenase (G-6-PDH)

p-Aminolidocainehemisuccinamide prepared in accordance with Examples 1 to 6 of Japanese Patent Application (OPI) No. 108904/78 was bound to G-6-PDH in accordance with Example 15 of the same application.

(3-2) Binding of p-aminolidocainehemisuccinamide and bovine serum albumine (BSA)

Binding was performed in accordance with Example 10 of Japanese Patent Application No. 108904/78. With the thus obtained product, the hapten value was determined by the IR method as 12.

Using the thus obtained product, rabbits were immunized in a conventional manner to prepare anti-lidocaine serum.

(3-3) Multilayer analysis film for measurement of lidocaine

A multilayer analysis film was prepared in a manner similar to Example (1-4).

(1) Water absorbing layer:
same as in Example (1-4)

(2) Detection layer:
same as in Example (1-4)

(3) Light shielding layer:
same as in Example (1-4)

(4) Reaction layer:
A glass fiber filter paper (Toyo Filter Paper GA-100, manufactured by Toyo Filter Paper Co., Ltd.) having a thickness of 100 μm was cut into 1 cm squares and impregnated with a mixture of the anti-lidocaine serum obtained in Example (3-2)—which had previously been diluted with a 0.05M tris chloride buffer (pH 5.0) containing 0.5% of BSA—glucose-6-phosphoric acid and an aqueous solution of NAD as a coenzyme. Thereafter, freeze drying was performed at $10^{-3}$ mm Hg (about −20° to about −40° C.). The freeze dried material was cut into 2 cm square and laminated on the light shielding layer at the center thereof, the surface of which had been wet with water.

(5) Reagent layer:
The G-6-PDH-labelled lidocaine prepared in Example (3-1) was dissolved in a 0.05M tris chloride buffer (pH 7.9) containing 0.5% of BSA. A glass fiber filter paper (Toyo Filter Paper GA-100, manufactured by Toyo Filter Paper Co., Ltd.) cut into 1 cm squares was impregnated with the solution followed by freeze drying. Thereafter, the freeze dried material was laminated on the reaction layer.

(3-4) Preparation of calibration curve using standard lidocaine solutions

Lidocaine hydrochloride was dissolved in 0.05M PBS (PH 7.3) to obtain solutions having lidocaine contents of 1, 2, 4, 6, 8 and 10 μg/ml.

From each of the sample solutions, 20 μl was taken and 1000 μl of PBS was added thereto to dilute again. From each of the dilutions, 140 μl was taken and dropped onto the multilayer analysis film prepared in Example (3-3). After the dropping, the film was allowed to stand for 10 minutes and then an intensity of reflected fluorescence was measured from the support side (excitation wavelength, 340 nm; fluorescence wavelength, 460 nm). Quantitative results as shown in Table 4 were obtained.

TABLE 4

| Lidocaine Content (μg/ml) | 0 | 1.0 | 2.0 | 4.0 | 6.0 | 8.0 | 10.0 |
|---|---|---|---|---|---|---|---|
| Relative Intensity of Fluorescence | 10.5 | 22.3 | 39.1 | 65.0 | 84.2 | 90.8 | 100 |

EXAMPLE 4

(4-1) Preparation of multilayer analysis film for measurement of $T_4$ using an inhibitor (1) Reaction layer:

A reaction layer containing anti-thyroxine serum and 8-anilinonaphthalenesulfonic acid was prepared in a manner similar to Example (1-4).

(2) Water absorbing layer:
same as in Example (1-4)

(3) Detection layer:

A 5% gelatin solution containing $10^{-10}$M of acetylcholinesterase and $5\times10^{-4}$M of 5,5'-dithiobis(2-nitrobenzoic acid) was coated and the coated layer dried to form a detection layer in a dry thickness of 10 μm.

Onto a colorless transparent polyethylene terephthalate film (thickness, 148 μm), the layers described above were coated or laminated in the order of (2), (3) and (1) to prepare a multilayer analysis film for the measurement of $T_4$.

(4-2) Measurement of $T_4$ using the film obtained in Example (4-1)

Reagent 1: reagent obtained by dissolving $10^{-3}$M of acetylthiocholine in a 0.1M phosphate buffer (pH 7.0) containing 0.1% bovine serum albumin Reagent 2: reagent obtained by dissolving Compound I described below (prepared in accordance with Example V of Japanese Patent Application (OPI) No. 104869/80) in a 0.1M phosphate buffer (pH 7.0) containing 0.1% bovine serum albumin in a concentration of $1.0\times10^{-7}$M.

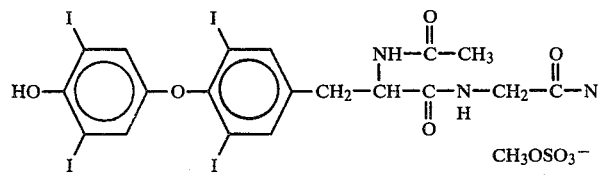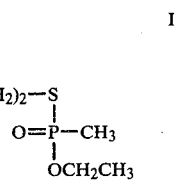

Sera containing thyroxine in various concentrations ($10^{-8}$ to $10^{-6}$M)—which were obtained by mixing serum with a solution of thyroxine in a 0.1M phosphate buffer of pH 7 in a desired concentration—were mixed, respectively, with 100 μl each of Reagent 1 and Reagent 2. From each of the mixtures, 150 μl was taken and dropped onto the multilayer analysis film prepared in Example (4-1), respectively. The film was incubated at 37° C. After the dropping, reflection density was measured at 410 nm 5 and 20 minutes after to read a difference between the measurement values.

Results obtained are shown in Table 5.

TABLE 5

| Concentration of Thyroxine (M) | Difference in Reflection Density |
|---|---|
| $1 \times 10^{-8}$ | 0.510 |
| $3 \times 10^{-8}$ | 0.473 |
| $9 \times 10^{-8}$ | 0.459 |
| $2.5 \times 10^{-7}$ | 0.405 |
| $5.0 \times 10^{-7}$ | 0.342 |
| $1.0 \times 10^{-6}$ | 0.285 |

Difference in reflection density = (reflection density 20 mins. after the dropping) - (reflection density 5 mins. after the dropping)

As is apparent from Table 5, a good calibration curve could be prepared in accordance with the method of this invention.

EXAMPLE 5

Glass fiber filter paper impregnated with a 0.1M phosphate buffer (pH 7.0) containing $10^{-3}$M of acetylthiocholine, $10^{-7}$M of Compound I described in Example (4-2) and 0.1% of bovine serum albumin in a proportion of 100 μl/cm² was freeze dried to prepare a reagent layer.

The thus obtained reagent layer was laminated onto the reaction layer of a multilayer analysis film having a layer structure as shown in Example (4-1) to prepare an integral type analysis film.

Onto the analysis film thus prepared, mixtures of 10 μl of sera containing thyroxine in various concentrations and 150 μl of a 0.1M phosphate buffer (pH 7.0) containing 0.1% of bovine serum albumin were dropped, respectively. The film was incubated at 37° C. for about 20 minutes. In this case, a good calibration curve as was observed in Example (4-2) was obtained.

EXAMPLE 6

Preparation of reaction layer containing particulate material

Agarose A-50 m (manufactured by Biorad Labs., 0.5 ml in wet volume) was mixed with a 0.05M phosphate buffer (pH 7.4) containing two sheets of glass fiber filter paper (manufactured by Toyo Filter Paper Co., Ltd., GA-200, 5.5 cm, the glass fiber filter paper was thoroughly untwisted in advance using a homoblender) and 30 ml of 0.1% of bovine serum albumin. The mixture was subjected to suction filtration on Nutze and corrected to a circular shape having a 7 cm diameter followed by drying. Thus, a porous material for a reaction layer was obtained. Then, the porous material was impregnated with a 0.05M phosphate buffer (pH 7.4) containing a 0.9% sodium chloride aqueous solution which contained anti-thyroxine serum and 8-anilinonaphthalenesulfonic acid, in a proportion of 150 μl/cm² of the buffer. After freeze drying, a reaction layer was obtained.

A multilayer analysis film was obtained with the same layer structure as in Example (4-1) by the procedure of Example (4-1) except that the reaction layer prepared above was replaced for the reaction layer prepared in Example (4-1).

Using the thus prepared multilayer analysis film, $T_4$ was measured as in Example (4-2). Based on the data obtained, a good calibration curve in response to thyroxine concentration could be prepared.

EXAMPLE 7

On the reagent layer of the multilayer analysis film prepared in Example 6, the reagent layer prepared in Example 5 was laminated to obtain an analysis film.

Using the analysis film thus prepared, $T_4$ was measured as in Example (4-2). Based on the data obtained, a good calibration curve in response to thyroxine concentration could be prepared.

EXAMPLE 8

The anti serum prepared in accordance with the method of Example (1-3) was purified with thyroxine-fixed agarose (manufactured by Miles Labs.). The thus purified anti serum was fixed in a conventional manner (see *Lectures on Biochemical Experiment*, subtitled "Chemistry of Protein", second separate volume, page 321, edited by Biochemical Association, Japan, published by Tokyo Kagaku Dojin) to Agarose A-50 m (manufactured by Biorad Labs.) which had been activated with BrCN to obtain agarose beads having a uniform concentration of the antibody. A predetermined amount of the agarose beads was mixed with glass fiber filter paper and the mixture was dried to obtain a reaction layer (which had an antityroxine IgG concentration of $10^{-9}$ mol/cm$^2$ of the reaction layer).

A multilayer analysis film for measurement of $T_4$ was obtained as in Example (4-1) except that the reaction layer prepared above was employed.

Using this multilayer analysis film, $T_4$ was measured in accordance with the method as described in Example (4-2).

From the data obtained, a good calibration curve for measurement of thyroxine was obtained similarly to Example (4-2).

EXAMPLE 9

On the reaction layer of the multilayer analysis film prepared in Example 8, the reagent layer prepared in Example 5 was laminated to obtain an analysis film.

Using the analysis film thus prepared, $T_4$ was measured as in Example (4-2). Based on the data obtained, a good calibration curve in response to thyroxine concentration could be prepared.

While the invention has been described in detail and with reference to specific embodiments thereof, it will be apparent to one skilled in the art that various changes and modifications can be made therein without departing from the spirit and scope thereof.

What is claimed is:

1. An analysis film for analyzing an analyte in an aqueous medium based on a competitive reaction in the presence of a fixed quantity of a protein which specifically binds with said analyte and a fixed quantity of a labeled analyte which is also reactive with said protein, said analysis film comprising a reaction layer having a void volume of 50 to 90% and a thickness of 200 μm to 1 mm which provides a liquid retention amount of at least 100 μl/cm$^2$ which is necessary for the analysis, wherein said reaction layer:
    (1) comprises a porous material,
    (2) contains a protein capable of specifically binding commonly with (a) said labeled analyte or its labeled analogue both being capable of modulating a signal produced by enzyme reaction as a result of a specific protein-binding reaction and with (b) said analyte, and,
    (3) does not substantially contain a complex of said analyte, or its analogue or said labeled analyte or its labeled analogue, with said protein.

2. The analysis film of claim 1 wherein said label is selected from the group consisting of an enzyme, an enzyme substrate, an enzyme substrate derivative, a prosthetic group of an enzyme, a coenzyme, an allosteric effector of an enzyme and an enzyme inhibitor.

3. The analysis film of claim 1 wherein said porous material is a fibrous porous material.

4. The analysis film of claim 3 wherein said fibrous porous material is a fibrous porous material having incorporated therein discrete particles.

5. The analysis film of claim 1 wherein a reagent layer containing said labelled analyte is further provided beneath said reaction layer.

6. The analysis film of claim 1 wherein a detection layer for receiving a detectable signal produced by the enzyme reaction is further provided beneath said reaction layer.

7. The analysis film of claim 6 wherein said reaction layer has an area smaller than that of said detection layer and is laminated on said detection layer so as not to project laterally from the detection layer.

8. The analysis film of claim 6 wherein a light-shielding layer is provided between said detection layer and said reaction layer.

9. The analysis film of claim 1 or claim 5 wherein a protein capable of specifically binding analyte or said its analogue thereof is incorporated into said reaction layer of said reagent layer by freeze drying.

10. In a method for analyzing analyte in an aqueous medium which comprises competitively reacting (a) said analyte in an aqueous medium, (b) a fixed quantity of a protein which specifically binds said analyte, and (c) a fixed quantity of a labeled analyte component, which is reactive with said protein, the method which comprises:
    (I) contacting an analysis film with a sample of the analyte-containing aqueous medium said analysis film comprising a reaction layer having a void volume of 50 to 90% and a thickness of 200 μm to 1 mm which provides a liquid retention amount of at least 100 μl/cm$^2$ which is necessary for the analysis, wherein said reaction layer:
        (1) comprises a porous material,
        (2) contains a protein capable of specifically binding commonly with said labeled analyte component being capable of modulating a signal produced by enzyme reaction as a result of a specific protein-binding reaction and with said analyte, but,
        (3) does not contain a complex of said analyte, an analogue thereof or said labeled analogue thereof with said proein,
    (II) competitively reacting said analyte with said protein in said reaction layer in the presence of said labeled analyte component capable of modulating a detectable signal as a result of a specific protein-binding reaction,
    said detectable signal being produced by enzyme reaction, and,
    (III) directly measuring said modulated signal by said competitive reaction.

11. The method of claim 10 wherein said label is selected from the group consisting of an enzyme, an enzyme substrate, an enzyme substrate derivative, a prosthetic group of an enzyme, a coenzyme, an allosteric effector of an enzyme and an enzyme inhibitor.

12. The method of claim 10 wherein said porous material is a fibrous porous material.

13. The method of claim 12 wherein said fibrous porous material is a fibrous porous material having incorporated therein discrete particles.

14. The method of claim 10 wherein a reagent layer containing said labelled analyte component is further provided beneath said reaction layer.

15. The method of claim 10 wherein a detection layer for receiving a detectable signal produced by enzyme reaction is further provided beneath said reaction layer.

16. The method of claim 15 wherein said reaction layer has an area smaller than that of said detection layer and is laminated on said detection layer so as not to project laterally from the detection layer.

17. The method of claim 15 wherein a light-shielding layer is provided between said detection layer and said reaction layer.

18. The method of claim 10 or claim 14 wherein a protein capable of specifically binding said analyte or said labelled analyte component is incorporated into said reaction layer or said reagent layer by freeze drying.

19. The analysis film of claim 1 wherein the reaction layer contains fine particles having a particle size of about 1 μm to about 1 mm selected from the group consisting of dextran, agarose, acrylamides and cellulose.

* * * * *